United States Patent
Rolland

(10) Patent No.: US 11,179,489 B2
(45) Date of Patent: Nov. 23, 2021

(54) SCENT DIFFUSER AND SCENT DIFFUSION DEVICE INCORPORATING SUCH A DIFFUSER

(71) Applicant: MAISON BERGER INNOVATION, Grandbourgtheroulde (FR)

(72) Inventor: Guillaume Rolland, Nantes (FR)

(73) Assignee: MAISON BERGER INNOVATION, Grand Bourgtheroulde (FR)

( * ) Notice: Subject to any disclaimer, the term of this patent is extended or adjusted under 35 U.S.C. 154(b) by 0 days.

(21) Appl. No.: 16/640,446

(22) PCT Filed: Aug. 22, 2018

(86) PCT No.: PCT/FR2018/052092
§ 371 (c)(1),
(2) Date: Feb. 20, 2020

(87) PCT Pub. No.: WO2019/038507
PCT Pub. Date: Feb. 28, 2019

(65) Prior Publication Data
US 2020/0171192 A1    Jun. 4, 2020

(30) Foreign Application Priority Data
Aug. 23, 2017 (FR) ........................................ 1757820

(51) Int. Cl.
*A61L 9/12* (2006.01)

(52) U.S. Cl.
CPC ......... *A61L 9/122* (2013.01); *A61L 2209/133* (2013.01)

(58) Field of Classification Search
None
See application file for complete search history.

(56) References Cited

U.S. PATENT DOCUMENTS 5,422,078 A * 6/1995 Colon ..................... A61L 9/12
239/54
5,935,526 A   10/1999 Moore
(Continued)

FOREIGN PATENT DOCUMENTS

| WO | 9004339 A1 | 5/1990 |
|----|------------|--------|
| WO | 20130211114 A1 | 2/2013 |

OTHER PUBLICATIONS

International Search Report for corresponding application PCT/FR2018/052092 filed Aug. 22, 2018; dated Nov. 30, 2018.

*Primary Examiner* — Jelitza M Perez
(74) *Attorney, Agent, or Firm* — Cantor Colburn LLP

(57) ABSTRACT

The invention relates to a scent diffuser (1) comprising a housing (2) having openwork parts (5), a substrate (6) housed inside the housing (2) and in which a fragrant substance or composition is adsorbed or absorbed, and means (7) for keeping the substrate (6) inside the housing (2). The housing (2) comprises a bottom (3) and a cover (4), one of the openwork parts (5) of the housing (2) is formed in the bottom (3) and the other is formed in the cover (4) of the housing (2), the substrate (6) is a block (61) provided with through-openings (62) through which an air flow that passes through the housing (2) is able to pass, and the means (7) for keeping the substrate (6) inside the housing (2) comprise first holding means (711, 712) made in one piece with the housing (2) and second holding means (721, 722) made in one piece with the substrate (6).

9 Claims, 4 Drawing Sheets

(56) References Cited

U.S. PATENT DOCUMENTS

| | | | |
|---|---|---|---|
| 6,511,531 B1* | 1/2003 | Cartellone | A61L 9/16 96/222 |
| 9,272,062 B1 | 3/2016 | Heflin | |
| 2010/0017597 A1 | 1/2010 | Chandwani | |
| 2013/0093108 A1 | 4/2013 | Scolari | |
| 2016/0263265 A1* | 9/2016 | Fantuzzi | B01F 3/04085 |
| 2016/0271287 A1* | 9/2016 | D'Amico | A61L 9/042 |

* cited by examiner

SCENT DIFFUSER AND SCENT DIFFUSION DEVICE INCORPORATING SUCH A DIFFUSER

FIELD OF THE INVENTION

The invention relates to a scent diffuser and a scent diffusion device incorporating such a diffuser.

It relates more particularly to a scent diffuser comprising a case with openwork portions, a substrate housed inside the case and wherein a fragrant substance or composition is adsorbed or absorbed, and means for holding the substrate inside of the case.

PRIOR ART

Scent diffusers also called perfume diffusers are known, as illustrate for example the document WO 9004339, the document EP 2 739 321 or the document US2010/017597. All these diffusers are characterised by their complexity, particularly their large number of parts, resulting in a significant assembly time. Furthermore, it is known that the substrate, in the case of a simple presentation, for example in the shape of a plate, tends to deform during, for example, the desorption of the fragrant composition or substrate. However, the solutions proposed today do not take into account this deformation of the substrate over time, this deformation can have an impact on the diffusion quality.

PURPOSE AND SUMMARY

A purpose of the invention is to provide a scent diffuser whose design allows mounting in a short time without affecting the diffusion quality over time.

Another purpose of the invention is to propose a scent diffuser, whose design allows a production with an extremely reduced number of parts.

To this end, the object of the invention is a scent diffuser comprising a case with openwork portions, a substrate housed inside the case and wherein a fragrant substance or composition is adsorbed or absorbed and means for holding the substrate inside the case, characterised in that the case comprises a bottom and a cover, in that the openwork portions of the case are formed, one in the bottom and the other, in the cover of the case, in that the substrate is a plate provided with through openings capable of being traversed by an air flow traversing the case and in that the means for holding the substrate inside the case comprise first holding means made integrally with the case and second holding means made integrally with the substrate.

The presence of means for holding the substrate inside the case allows controlling the deformation, in particular by loss of volume, of the substrate which can result in particular from the desorption of the fragrant composition or substance.

Making the holding means integrally with the case or with the substrate allows simplifying the manufacture and reducing the number of parts.

The choice of a substrate in the shape of a perforated plate allows a simple design of the holding means.

According to one embodiment of the invention, at least one portion of the second holding means is present at least in duplicate, that is to say in at least two portions of the second holding means on the substrate, each portion of the second holding means being capable of selectively cooperating with at least one portion of the first holding means.

The presence of at least one portion of the holding means in at least two copies allows multiplying the number of allowable positions of the substrate inside the case. This results in less reflection time for the operator who performs the assembly and a reduced risk of error.

According to one embodiment of the invention, at least one portion of the first holding means comprises an element protruding from the openwork portion of the bottom or of the cover of the case and at least one portion of the second holding means is formed by one of the through openings of the plate constituting the substrate.

According to one embodiment of the invention, the means for holding the substrate inside the case are configured to delimit at least two areas for holding the substrate inside the case. This results in a more secure holding of the substrate even after deformation of the substrate resulting from a loss of volume.

According to one embodiment of the invention, one of the holding areas is disposed in the central portion of the plate constituting the substrate.

According to one embodiment of the invention, in the holding area disposed in the central portion of the plate constituting the substrate, the first holding means have the shape of a pad or stud protruding from the openwork portion of the bottom or of the cover of the case and the second holding means are formed by one of the through openings of the plate constituting the substrate, this through opening being formed in the central portion of the plate constituting the substrate.

According to one embodiment of the invention, one of the holding areas is disposed at the periphery of the plate constituting the substrate.

According to one embodiment of the invention, in the holding area disposed at the periphery of the plate constituting the substrate, the first holding means have the shape of a tenon protruding from the openwork portion of the bottom or of the cover of the case and the second holding means are formed by one of the through openings of the plate constituting the substrate, this through opening being formed in the peripheral portion of the plate constituting the substrate to form a notch inside which the tenon is capable of being at least partially inserted.

According to one embodiment of the invention, at least one portion of the through openings of the plate constituting the substrate has a hexagonal shape. The hexagonal shape of the openings ensures an improved diffusion quality.

According to one embodiment of the invention, the substrate is a plate made of polymer, preferably made of thermoplastic elastomer.

According to one embodiment of the invention, the scent diffuser comprises an identification means housed inside the case. Such an identification means can allow, for example, monitoring the duration and/or the frequency of use of the diffuser.

Also, the object of the invention is a scent diffusion device comprising a scent diffuser, a fluid circulation circuit, a housing for receiving the scent diffuser disposed on said fluid circulation circuit, and means for forced air circulation through said fluid circulation circuit, characterised in that the scent diffuser is of the aforementioned type.

BRIEF DESCRIPTION OF THE FIGURES

The invention will be better understood upon reading the following description of exemplary embodiments, with reference to the appended drawings wherein.

DETAILED DESCRIPTION

Figure 1:
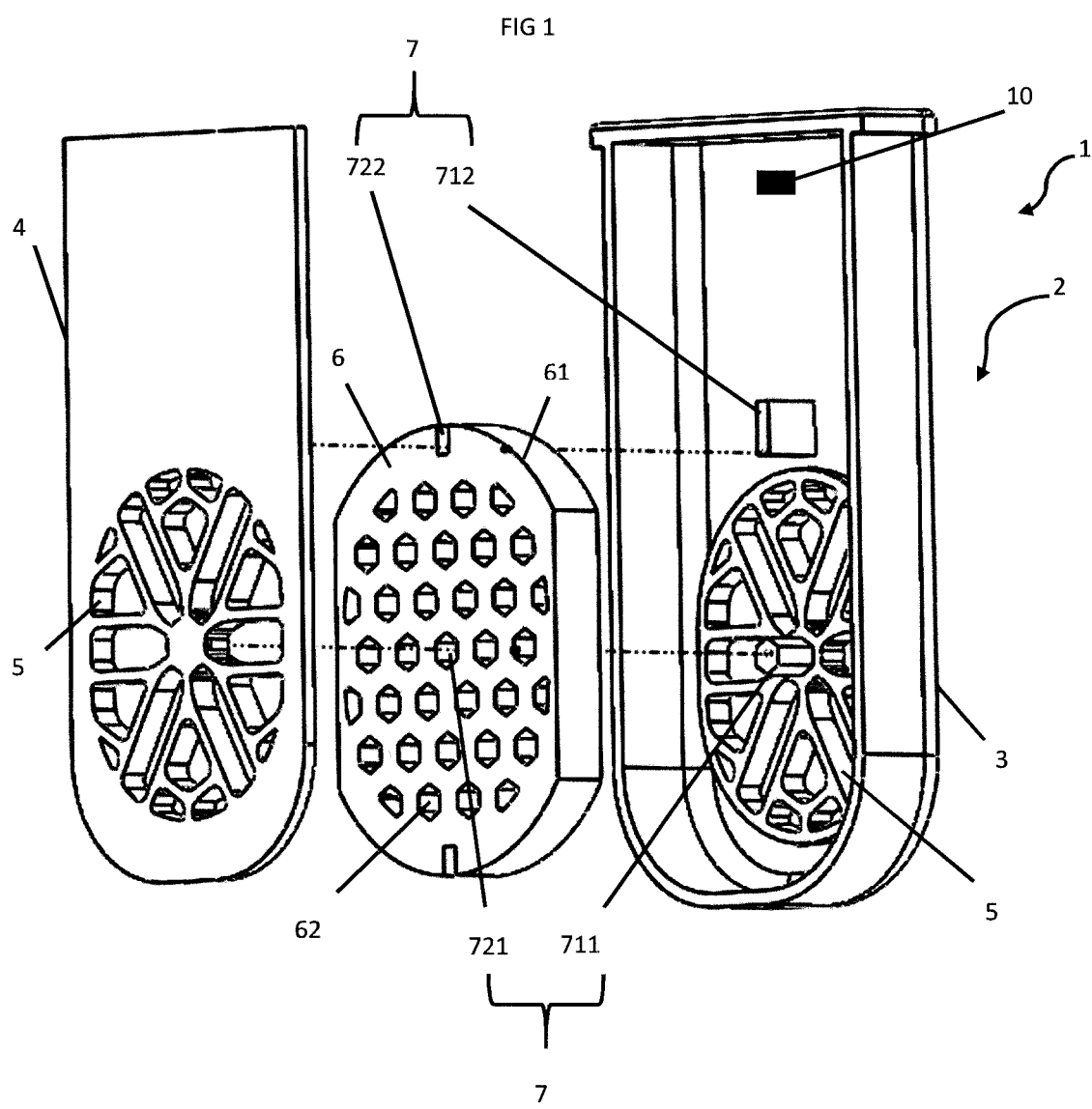
FIG. 1 shows a perspective view in exploded position of the elements constituting a diffuser according to the invention.
Figure 2:
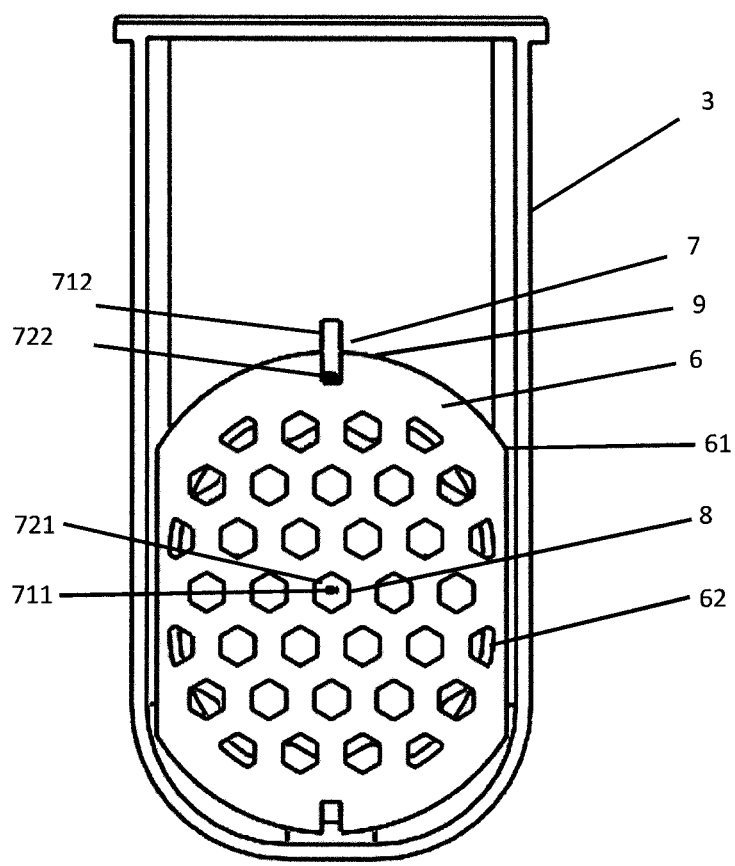
FIG. 2 shows a view taken on the cover side of the case of a diffuser in accordance with the invention in the state removed from the cover to allow viewing the inside of the case.
Figure 3:
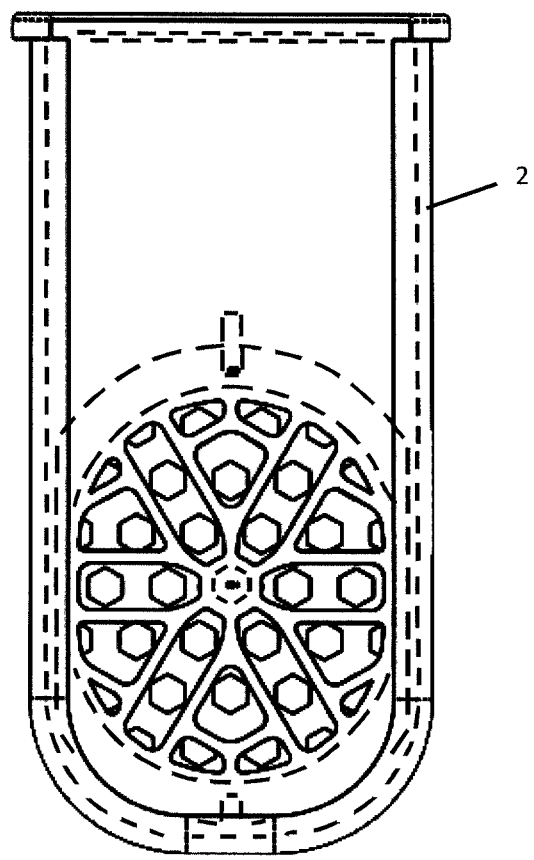
FIG. 3 shows a front view of a diffuser in accordance with the invention with, in dashed lines, the hidden lines.
Figure 4:
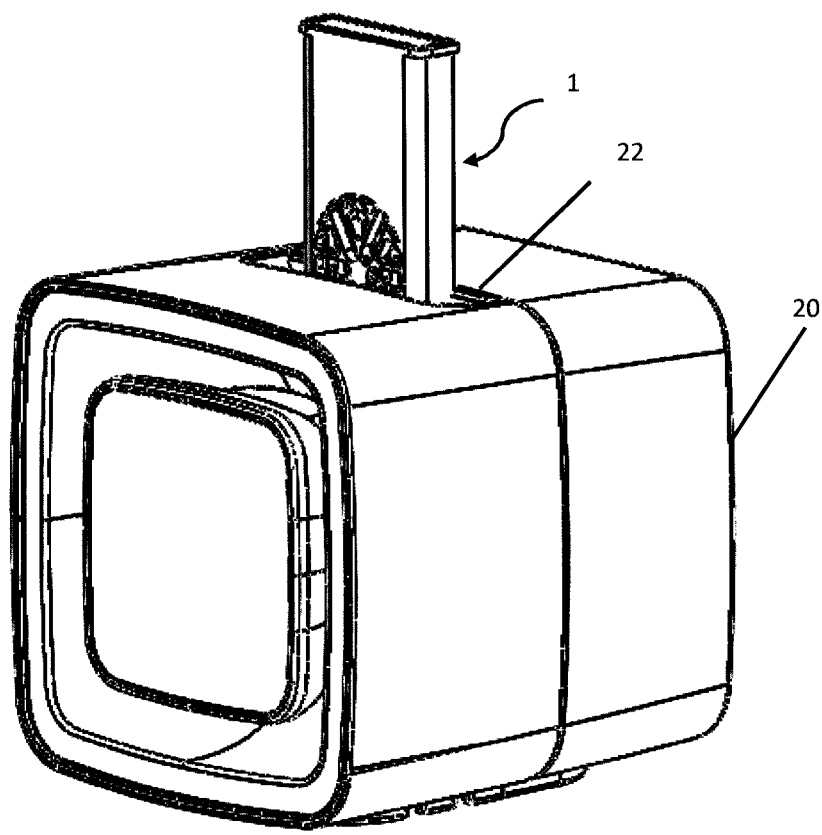
FIG. 4 shows a perspective view of a scent diffusion device during the insertion of a diffuser into the device.
Figure 5:
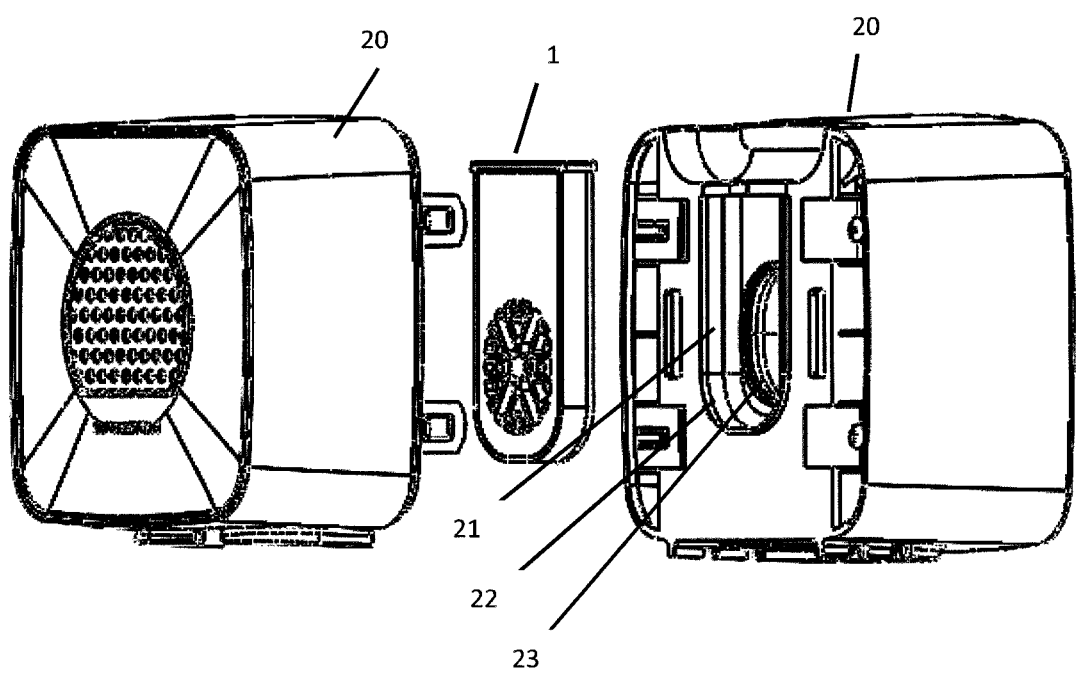
FIG. 5 shows a perspective view of a scent diffusion device in the exploded state of the elements constituting it.

As mentioned above, the object of the invention is a scent diffuser, the scent diffusion of which can take place passively in contact with air or via a scent diffusion device 20 of the type shown in FIGS. 4 and 5.

Such a scent diffuser 1 comprises a case 2 with openwork portions 5, a substrate 6 housed inside the case 2 and wherein a fragrant substance or composition is adsorbed or absorbed, and means 7 for holding the substrate 6 inside the case 2. The case 2, shown here in a quadrangular shape, comprises a bottom 3 and a cover 4 which can be assembled together, preferably by snap-fitting. Generally, the bottom 3 and the cover 4 are made of synthetic material. The bottom 3 comprises an openwork portion 5 just like the cover 4. Each time, the openworks are formed by through openings. The openwork portions 5 of the bottom 3 and the cover 4 are disposed facing one another in the closed state of the case 2 to facilitate an air circulation through the case 2. These openwork portions 5 form here at each time a circular surface with at least one portion of the openworks disposed in a radiating disposition inside said surface. The substrate 6, in turn, is in the form of a plate 61 provided with through openings 62. The through openings 62 of the plate 61 constituting the substrate 6 are of a hexagonal shape. These openings 62 extend between the openwork portions 5 in the inserted state of the substrate 6 into the case 2. In the example shown, the substrate 6 is a polymer plate. This polymer is a thermoplastic elastomer, particularly a polyether block amide (PEBA). As an example, the polymers of the PEBAX trademark (registered trademark) are completely adapted for such use.

A fragrant composition or substance is adsorbed on the plate. This adsorption was, in the example shown, carried out by soaking the plate in a bath of fragrant substance or composition.

Such a preparation of the substrate is well known to those versed in this art. The substrate could also have been produced by absorption of the fragrant composition or substance on the plate.

The scent diffuser 1 also comprises means 7 for holding the substrate inside the case 2. These holding means 7 tend to prevent the substrate 6 from freely moving inside the case 2 throughout the desorption phase thereof. Indeed, during the desorption phase thereof, the substrate 6 is caused to lose 15 to 20% of its volume, then causing this substrate 6 to be deformed. The holding means 7 comprise first holding means made integrally with the case and, shown in 711 and 712 in the figures, and second holding means made integrally with the substrate 6 and, shown in 721 and 722 in the figures. These first and second holding means are intended to cooperate with each other in the inserted state of the substrate 6 inside the case, in the closed position of the case 2.

In the examples shown, the means 7 for holding the substrate inside the case are configured to delimit two areas 8, 9 for holding the substrate 6 inside the case 2. Particularly, in the example shown, one of the holding areas 8, 9, called first holding area 8, is disposed in the central portion of the plate 61 constituting the substrate 6, and the other of the holding areas 8, 9, called second holding area 9, is disposed at the periphery of the plate 61 constituting the substrate 6. Obviously, the number of holding areas can be increased without departing from the scope of the invention.

In the example shown, in the first holding area 8, the first holding means 711 has the shape of a pad or stud protruding from the openwork portion 5 of the bottom 3 of the case 2 and the second holding means 721 are formed by one of the through openings 62 of the plate 61 constituting the substrate 6, this through opening 62 being formed in the central portion of the plate 61 constituting the substrate 6.

In the second holding area 9, the first holding means 712 have the shape of a tenon protruding from the openwork portion 5 of the bottom 3 of the case 2 and the second holding means 722 are formed by one of the through openings 62 of the plate 61 constituting the substrate 6, this through opening 62 being formed in the peripheral portion of the plate 61 constituting the substrate 6 to form a notch inside which the tenon is capable of being at least partially inserted. This notch is open in the direction of the section or edge of the plate constituting the substrate, that is to say in the direction of the plate portion connecting the faces of the plate together. Indeed, generally, at least one portion of the first holding means 711, 712 comprises an element protruding from the openwork portion 5 of the bottom 3 or of the cover 4 of the case 1 and at least one portion of the second holding means 721, 722 is formed by one of the through openings 62 of the plate 61 constituting the substrate 6.

To save installation time, in the example shown, a portion 722 of the second holding means 721, 722 is present at least in duplicate, that is to say in at least two copies on the substrate 6, each copy being capable of selectively cooperating with at least one portion of the first holding means 711, 712. Indeed, the plate 61 constituting the substrate 6 comprises two notches arranged on two opposite rims of the plate. This plate is thus a reversible plate which can rest against the bottom of the case by either one of its faces and can be inserted into the case in a first angular position or in a second angular position offset by 180° relative to the first angular position.

To complete the assembly, the scent diffuser may comprise an identification means 10 housed inside the case 2. This identification means 10 may for example be formed by a radio frequency identification (RFID) tag, this tag comprising an RFID chip and an antenna. This identification means allows communication by wireless link with a remote unit which can be integrated into the diffusion device 20 associated with the diffuser. Thanks to this identification means, it may be possible to monitor the duration and/or the frequency of use of the scent diffuser to allow its replacement in good time.

The method for mounting the scent diffuser, as described above, is extremely simple. It suffices to insert in a flat manner the plate 61 constituting the substrate 6 into the bottom 3 of the case so that the central opening 62 of the plate is traversed by the pad protruding from the bottom of the case and the notch partially surrounds the tenon. Once the plate constituting the substrate in position, it suffices to close the case by assembling the cover of the case to the bottom of the case, this assembly being performed here by snap-fitting. The scent diffuser is then stored in a hermetic sealed packaging until its first use. Before the first use, this packaging is removed. This packaging can be reused to hermetically keep the scent diffuser again thanks to a hook-and-loop closure or simply a fold on the top of the packaging. This diffuser may be intended for a diffusion device 20, as shown in FIGS. 4 and 5. This diffusion device 20 is here in the form of a block which internally comprises a circuit 21 for circulation of fluid traversing said block, a housing 22 for receiving the scent diffuser 1 disposed on said fluid circulation circuit 21 and means 23 for forced air circulation through said fluid circulation circuit 21. The forced air circulation means 23 are formed here by a fan. The diffuser is therefore, after removing the hermetic packaging thereof, inserted into the housing 22 of the scent diffusion device 20, as shown in FIG. 4. It is noted that the case has two opposite rims converging towards the end of introduction of the case into the housing to facilitate the insertion thereof into the housing. The end of the case, opposite to the end of introduction of the case into the housing is in turn provided with an external peripheral shoulder forming a stop for limiting the introduction of the case into the diffuser and a sealing lip.

The invention claimed is:

1. A scent diffuser comprising:
a case with axially extending openwork portions;
a substrate housed inside the case in which a fragrant substance or composition is adsorbed or absorbed; and
means for holding the substrate inside the case;
wherein the case comprises a bottom and a cover, the openwork portions of the case being formed one, in the bottom, and the other, in the cover, of the case;
wherein the substrate is a plate provided with axially extending through openings capable of being traversed by an air flow axially traversing the case and;
wherein the means for holding the substrate inside the case comprise first holding means made integrally with the case and second holding means made integrally with the substrate, the means for holding the substrate inside the case being configured to delimit at least two areas for holding the substrate inside the case, one of the holding areas being disposed in a central portion of the plate constituting the substrate and another holding area being disposed at a periphery of the plate constituting the substrate, the first holding means having a shape of two tenons protruding axially from the openwork portion of the bottom or of the cover of the case and each one cooperating with the second holding means made integrally with the substrate;
wherein the second holding means are formed by at least two axially extending through notches of the plate constituting the substrate, the through notches being formed respectively in the central portion and the peripheral portion of the plate constituting the substrate and each one forming a notch inside which an associated one of said tenons is capable of being at least partially axially inserted.

2. The scent diffuser according to claim 1, wherein the second holding means comprises two portions on the substrate, each portion of the second holding means being capable of selectively cooperating with at least one portion of the first holding means.

3. The scent diffuser according to claim 1, wherein at least one portion of the first holding means comprises an element protruding from the openwork portion of the bottom or of the cover of the case, and at least one portion of the second holding means is formed by one of the through openings of the plate constituting the substrate.

4. The scent diffuser according to claim 3, wherein one of the holding areas is disposed in the central portion of the plate constituting the substrate.

5. The scent diffuser according to claim 4, wherein, in the holding area disposed in the central portion of the plate constituting the substrate, the first holding means have the shape of a pad or stud protruding from the openwork portion of the bottom or of the cover of the case and the second holding means are formed by the one of the through openings of the plate constituting the substrate, this through opening being formed in the central portion of the plate constituting the substrate.

6. The scent diffuser according to claim 1, wherein at least one portion of the through openings of the plate constituting the substrate has a hexagonal shape.

7. The scent diffuser according to claim 1, wherein the substrate is a plate made of polymer.

8. The scent diffuser according to claim 1, further comprising an identification means housed inside the case.

9. A scent diffusion device comprising a scent diffuser, a fluid circulation circuit, a housing for receiving the scent diffuser disposed on said fluid circulation circuit, and means for forced air circulation through said fluid circulation circuit, wherein the scent diffuser is in accordance with claim 1.

* * * * *